United States Patent [19]

Lavie et al.

[11] Patent Number: 5,049,589
[45] Date of Patent: Sep. 17, 1991

[54] ANTIVIRAL AEROSOL COMPOSITIONS AND PRESSURIZED CONTAINERS CONTAINING SAME

[75] Inventors: David Lavie; Michel Revel; Dalia Rotman, all of Rehovot, Israel; Vincent Vande Velde, Brussels, Belgium

[73] Assignee: Yeda Research and Development Company, Ltd., Rehovot, Israel

[21] Appl. No.: 452,436

[22] Filed: Dec. 19, 1989

Related U.S. Application Data

[62] Division of Ser. No. 82,700, Aug. 7, 1987, Pat. No. 4,898,891.

[30] Foreign Application Priority Data

Aug. 8, 1986 [IL] Israel .......................................... 79661

[51] Int. Cl.$^5$ ..................... A01N 31/08; A01N 31/045; A01N 25/02; A61K 9/14
[52] U.S. Cl. ..................................... 514/732; 514/738; 424/43; 424/45; 252/308; 252/311
[58] Field of Search ................. 514/732, 738; 252/305, 252/306, 307, 308, 309, 310, 311, 312, 313.1; 424/400, 43, 45

[56] References Cited

FOREIGN PATENT DOCUMENTS 59-190921 10/1984 Japan .

OTHER PUBLICATIONS

Halm, Gyogyszerészet: Bulletin of Pharmacy, 33, 217–218, 1978.
Mishenkova et al, "Antiviral properties of St. John's Wort and Preparations produced from It" Chem. Abstracts 85: 187161y.
Derbentseva et al, "Effect of Tannins from *Hypericum perforatum* on influenza Viruses", Chem. Abstracts 78: 67532d.
Brockman et al., "Isolation and Constitution of Pseudohypericin", *Cehmical Abstracts*, 81:528 (1974).
Brockman et al., "Constitution of Pseudohypericin", *Chemical Abstracts*, 139833k:(1), 37–40 (1975).
Muldner, "Antidepressive Effect of a Hypericum Extract Standardized to the Active Hypericin Complex; Biochemistry and Clinical Studies", Embase Abstract No. 84174869, (1984).
Okpanyi et al, "Experimental Animal Studies of the psychotropic activity of a Hypericum Extract", *Chemical Abstracts*, 106:113450x (1987).
Song et al, "Proton Release from Stentor Photoreceptors in the Excited States", *Biophys. J.*, 35:551–555 (1981).
Neumann, H. "Skin food with New active substances", *Chemical Abstracts*, 66:88613y (1967).
Brockmann, H. et al, "Zur Kenntnis des Hypericins und Pseudo–Hypericins", *Chemical Abstracts* 52:16317f (1958).
Brockman, H. et al, "Totalsynthese des Hypericins", *Chemical Abstracts*, 52:10039h, (1958).
Merck index, Eighth edition, Stecher, O. G., editor, 1968, p. 558, "Hypericin".
Daniel, K. "Further Communications on the Photodynamic Substance, Hypericin", *Chemical Abstracts*, 46:9721e, (1952).
Adamsky, R. et al, "Stability of hypericin in juice, dry extract, and tablets from *Hypericum perforatum plants*", *Chemical Abstracts*, 75:91286k (1971).
Harry, R. G., "Cosmetic Materials" vol. 2, 1963, Cheimcal Publishing Co., Inc., N.Y., N.Y. pp. 352–353.
Merck Index, 10th edition, 1983, p. 710, Merck & Co., Inc., Rahway, NJ.
Meruelo, D. et al, "Therapeutic agents with dramatic antiretroviral activity and little toxicity at effective doses: Aromatic polycyclic diones hypericin and pseudohypericin" Proc. Acad. Sci. U.S.A., vol. 85, No. 14, Jul. 1988, pp. 5230–5234.

*Primary Examiner*—Nathan M. Nutter
*Attorney, Agent, or Firm*—Browdy and Neimark

[57] ABSTRACT

The invention relates to antiviral compositions of matter containing as active ingredient hypericin or pseudohypericin. The novel compositions are of special use in the treatment of, and alleviation of symptons of various diseases caused by viruses such as vesiculr stomatitis, influenza, herpes simplex, HSV-1 and HSV-2. The mode of activity seems to be by inhibition of RNA synthesis and interfering with virus replication. The pharmaceutical compositions can be applied by a variety of routes. Topical applications have proved to be effective against a variety of viral afflictions.

8 Claims, 4 Drawing Sheets

ANTIVIRAL AEROSOL COMPOSITIONS AND PRESSURIZED CONTAINERS CONTAINING SAME

This is a division of application Ser. No. 07/082,700 filed Aug. 7, 1987, now U.S. Pat. No. 4,898,891.

FIELD OF THE INVENTION

The invention relates to pharmaceutical compositions of matter which contain as active ingredient hypericin or pseudohypericin. The compositions are effective in inhibiting viral replication and thus bring about the gradual destruction of the virus. The compositions are of value in systemic as well as topical application. They can be used effectively against vesicular stomatitis virus, influenza virus, herpes simplex HSV-1, HSV-2 and others. The active ingredient can be isolated from the perennial plant *Hypericum triquetrifolium Turra* (or *Hypericum crispum L.*).

SUMMARY OF THE INVENTION

There are provided antiviral pharmaceutical compositions which contain as active ingredient hypericin or pseudohypericin. The compositions are effective in interfering with the development and replication of viruses in mammals, including humans, inducing their destruction, without any appreciable toxicity to the mammal.

BACKGROUND OF THE INVENTION

Only few compounds are known to possess antiviral activity. One of the best is interferon, which is currently in experimental therapeutic use in humans. The production and purification of human interferon is fairly tedious and the available quantities are limited. However, much is known today about the mechanism of action of this antiviral protein which acts by inducing an antiviral state in cells (Antiviral Drugs and Interferon: The molecular Basis of their Activity. Ed Yechiel Becker 1984, p. 357, Martinus Nijhoff Publishing Boston). The active ingredient, hypericin and pseudohypericin can be isolated and purified. The results of our investigation led to the isolation from the plant *Hypericum triquetrifolium* Turra, also known as *Hypericum crispum L.*, of two compounds identified chemically as hypericin (1) and pseudohypericin (2). These compounds have been isolated among others in a pure form and characterized using NMR techniques. Their spectra showed all the characteristic signals specific for their polycyclic aromatic structures.

(1)

(2)

These two compounds showed an unequivocal and strong antiviral activity against vesicular stomatitis virus (VSV), influenza virus, herpes simplex HSV-1 and HSV-2 and others. Their toxicity was found to be low in tissue cultures and in mammals. Tests performed on the incorporation of radioactive $^3H$-uridine into RNA by the virus-indicated that the activity of these two compounds involves an inhibition of RNA synthesis, interfering with the replication of the virus, resulting in its destruction.

In order to display their activity, the compounds have to be in direct contact with the virus. The estimation of the antiviral activity is based on protection of cells by the compounds from destruction by the virus, previously put in contact with low concentrations of the compounds tested.

In view of this behaviour the compounds are appropriate for topical application in localized infections.

The compounds have been described earlier by Brockmann et al. (H. Brockmann and W. Sanne. Zur Kenntnis des Hypericins und Pseudo-hypericins. Chem. Ber. 90, 2480, (1957)); H. Brockmann, U. Franssen, D. Spitzner and H. Augustiniak. Zur Isolierung und Konstitution des Pseudohypericins, Tetrahedron Letters, 1991, (1974)) who have also provided the appropriate NMR signals for each of the two compounds (1) and (2) (H. Brockmann and D. Spitzner. Die Konstitution des pseudohypericins, Tetrahedron Letters 37, (1975)). A synthesis for hypericin has also been reported (H. Brockmann, F. Kluge and H. Muxfeldt. Totalsynthese des Hypericins, Chem. Ber. 90, 2302 (1957)). Although species of the genus Hypericum (St. John's wort) have been reported to display an antiviral activity (N. A. Derbentseva et al., Effect of tannins from *Hypericum perforatum* on influenza virus Mikrobiol. Zh. (Kiev) 34, 768 (1972) C.A. 78 67532d; Mishenkova et al., Antiviral properties of St. John's wort and preparation produced from it. Tr. S'ezda Mikrobiol. Ukr. 4th. 222 (1975), C.A. 85 187161Y), the two compounds hypericin (1) and pseudohypericin (2) have never been reported or recorded to have antiviral activity.

Hypericin (1) is also described in the Merck Index (Eighth edition, O. G. Stecher Ed., 1968, p 558) as appearing to have a tonic and tranquilizing action on the human organism. It has been used in medicine as antidepressant (Daniel K. Further communication on the photodynamic substance hypericin. Hippokrates 20, 526 (1949); C.A. 46 9721/e (1952)).

CHEMICAL PREPARATION

Figure 1:
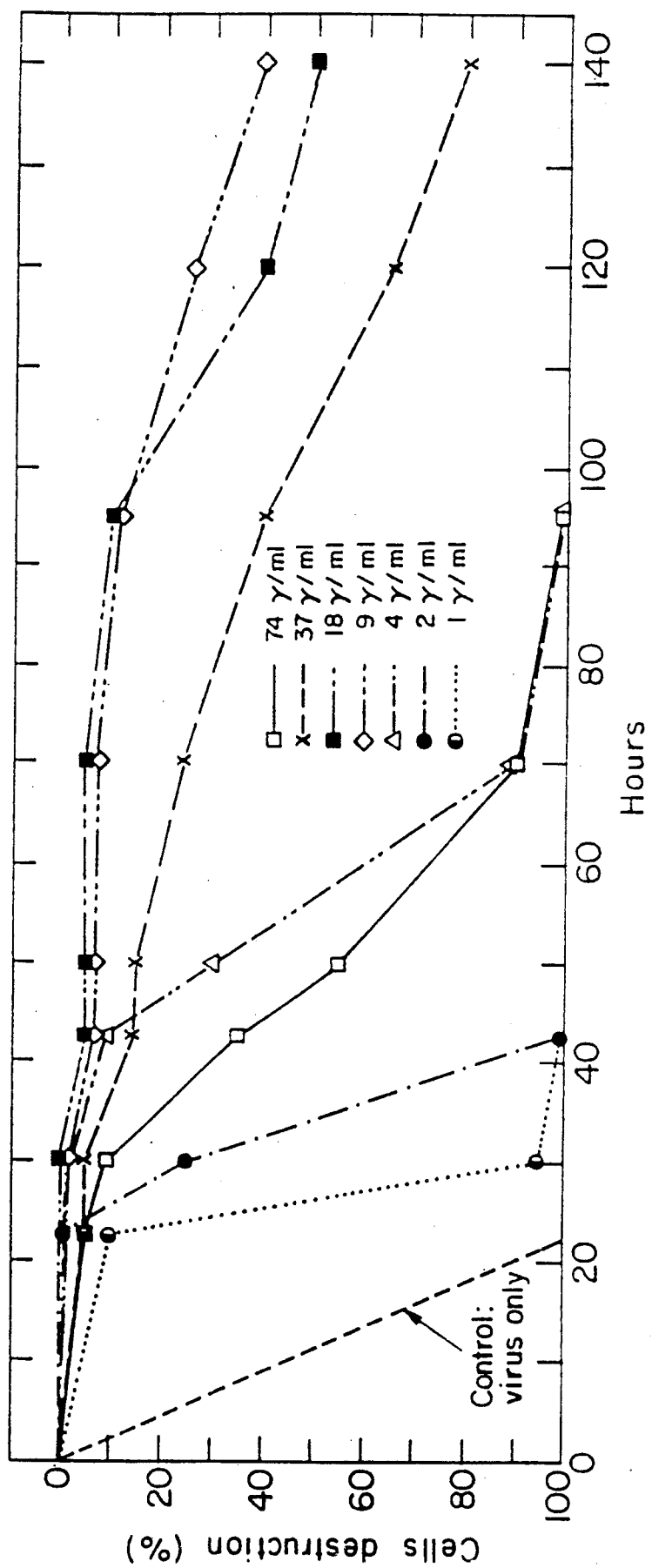
FIG. 1: Delay of destruction of VSV infected cells in presence of different concentrations of hypericin (1).

The herb of the whole plant harvested at its flowering time was dried at 55° C., cut and milled, and then extracted with acetone. 1 kg. of the material was put in a soxhlet and extracted for several hours (5-10 hr) until the extracting solvent was colorless. The solution assumed a red fluorescent color. The solvent was evaporated under reduced pressure to complete dryness of the residue (95 g). This residue was then fractionated on a chromatographic column, packed with silica gel 60 (0.06-0.20 mm). The chromatography applied was the dry process, whereby 25 g of the residue dissolved in acetone are added to an equal amount of silica gel 60 and evaporated on a rotavapor with swirling until homogeneous and dry. The mixture was then placed at the top of the column, (1/Kg) and eluted first with $CH_2Cl_2$ until the solvent reached the bottom of the column, followed by a solvent mixture consisting of $CH_2Cl_2$-acetone-MeOH 75:15:10 parts. When the red color became weaker, the concentration of the $CH_2Cl_2$ was reduced so as to form a solvent mixture consisting or 55:15:10 parts respectively. The fractions collected were of about 250 ml each; they were monitored on thin layer chromatoplates observing the $R_f$ value of the two main red fluorescent spots under ultraviolet light. The developing solvent mixture was as above. The chromatography was completed in about 2 days. Further purification and separation of the two main components was reached through flash chromatography using silica gel 60 (mesh 0.04-0.06) with slight pressure and again using the dry approach with the same solvent combination. The two main components of interest were identified as hypericin $R_f$ 0.45, yield 0.19 g and pseudohypericin $R_f$ 0.35, yield 0.73 g. NMR spectra identical with those reported in the literature (Brockmann (1975) ibid.).

BIO-ASSAYS

The antiviral tests were performed using the radioactive assay based on the incorporation of radioactive $^3$H-uridine into viral RNA in infected cells. The cell cultures used in these tests were grown on Eagle's medium and they originated from human fibroblast FS11 cultures established in our laboratory (J. Weissenbach, M. Zeevi, T. Landau and M. Revel. Identification of the translation products of human fibroblast interferon mRNA in reticulocyte lysates. Eur. J. Biochem., 98 1-8 (1979)). The virus used for these tests was vesicular stomatitis virus (VSV) proliferating on the cell cultures. In this test the antiviral activity is expressed as reduction in incorporation of labelled material, namely inhibition of viral replication. A simpler and more rapid method taking into consideration the toxicity of the tested compounds to the cells was the cytophathic effect (CPE) monitored in the cells under the microscope. This system enables to follow the effect of the antiviral compounds on the cells for a number of days. It was carried out using microtiter plates having 96 wells (8×12), and serial dilutions of the tested compounds were added in decreasing concentration in order to determine the activity against their toxicity at the lowest concentration. A relatively short incubation time (about 1 hr) following a contact between the virus and the tested dilution of the compound was allowed before adding to the cells in the wells, and then the cytopathic effect was recorded at time intervals. An additional assay system used was the inhibition of plaque formation by virus in a monolayer culture. Here, absence of plaque formation indicates inhibition of viral replication. This procedure was used in the case of influenza and herpes simplex. For the latter the following procedure was followed: serial dilutions of the hypericin and pseudohypericin solutions were prepared in PBS (phosphate buffered Saline). A constant amount of virus was added to each dilution, and the mixtures were incubated for several hours at 4° C., the mixtures were then used to infect monolayers of Vero cells in 60 mm dishes, in the plaque assay, as follows:

1. Adsorption of virus (in the mixture), 0.2 ml/plate, 1 hr 37° C.
2. Addition of overlay: 2% FCS (Fetal calf serum) in methyl cellulose or agarose. Incubation 3 days in a humidified $CO_2$ incubator (the virus mixture was not removed after the 1 hr adsorption). 3. Counting plaques after staining.

RESULTS

Vesicular stomatitis virus assays

Using the CPE method, the crude extract of the plant *H. crispum* showed activity at concentrations of 325 γ/ml. A first purification led to a mixture active at 85 γ/ml. At this stage the toxicity to the cells in the culture was highly reduced. Following the sequence of chromatographies described above the two compounds hypericin and pseudohypericin were obtained showing activity at a level of 5 γ/ml, see for example charts 1 and 2. Chart 1 indicates the delay in destruction of VSV infected cells at a concentration of a few gamma per ml of hypericin. At the optimum concentration of 9 γ/ml, the cells remained viable for time periods up to 140 hrs. Chart 2 shows that at the same concentrations the cells in contact with the products alone (without virus), remained viable throughout the same period of incubation.

For the radioactive bioassay the compound tested, pseudohypericin, was put into the assay system following a previous contact of the virus with different concentrations of the substance, and the mixture then added to the cell cultures. The results are plotted in charts 3 and 4. It can be seen that the decrease in percent $^3$H-uridine incorporation accounting for inhibition of the RNA synthesis is observed not only on the VSV infected cells, but also on the cells alone used as control. A definite dose response with the different dilutions was reached, and a nice repetition of the results could be observed with two virus dilutions $50 \times 10^6$ p.f.u./well and $100 \times 10^6$ p.f.u./well (p.f.u.=plaque forming unit) utilized for cell infection. It should be emphasized again that such an effect on RNA synthesis may provide the key for the activity of the compound on the virus and account for the action on the cells.

Assays using influenza virus

The plaque bioassays described above were carried out with influenza virus. A fraction consisting of a mixture of (1) and (2) was tested for activity on influenza virus A/Port-Chalmers/73. The results are collected in Table 1.

It can be seen that 96% of inhibition is obtained with a concentration as low as 0.15 μg/ml, when all concentrations above it show virus inhibition of 100%. The cells in the higher concentrations looked normal throughout the experiments. In a control experiment, similar concentrations of the same mixture were left in contact with the tissue cultures alone (uninfected) and they developed normally to produce the cells monolayers.

TABLE 1

In vitro plaque assay for a mixture of (1) and (2) with influenza virus

| Concentrations in ug/ml | 1.5 | 0.75 | 0.37 | 0.19 | 0.09 | Control |
|---|---|---|---|---|---|---|
| Number of plaques | 0 | 0 | 0 | 8 | 42 | 200 |
| Inhibition % | 100 | 100 | 100 | 96 | 79 | |

Assays with Herpes simplex virus, strain KOS (HSV-1)

In these experiments the concentration of the stock solutions was determined using a calibrated concentration curve prepared with ultraviolet light at 280 mm. The saturated solutions of the respective two compounds were filtered and the transmittance plotted on the curve for the determination of the concentration. Higher accuracy was thereby reached.

The results are given in Table 2 for the different dilutions. They show that hypericin was active at a concentration of 2.5 ng/ml ($10^{-9}$ gr) and pseudohypericin at a concentration of 472 ng/ml.

TABLE 2

Anti-viral activity of hypericin and pseudo-hypericin on Herpes simplex HSV-1

| | No. of plaques per plate | Inhibition (%) |
|---|---|---|
| Final concentration of hypericin | | |
| 250 ng/ml ($10^{-9}$gr) | 0 | 100 |
| 25 ng/ml | 0 | 100 |
| 2.5 ng/ml | 0 | 100 |
| 0.25 ng/ml | 1176 | 9 |
| 0 | 1288 | |
| Final concentration of pseudohypericin | | |
| 4720 ng/ml ($10^{-9}$gr) | 0 | 100 |
| 472 ng/ml | 1 | 100 |
| 47.2 ng/ml | 1488 | (−15) |
| 4.72 ng/ml | 1000 | 0 |
| 0 | 1288 | |

In view of the above it is apparent that compositions according to the invention are effective when they contain small amounts of the active ingredient. These are generally in the range of about 5 to 10 mg/kg of body weight.

Various forms of administration can be resorted to. For afflictions of the skin or of mucous membranes, they are advantageously used in topical forms such as lotions or ointments, for example in polyethylene glycol. These will typically contain from about 1 to 5% hypericin or from about 2 to 5% pseudohypericin weight per volume. The active principles, i.e., hypericin and pseudohypericin, may also be administered in combination in any desired ratio.

In addition to topical administration, any form of systemic administration can be used. The dosage of active principle should be such that a sufficient amount is present in the system to permit effectiveness against viruses upon contact therewith wherever they may be found in the system. While a certain amount of empirical experimentation will be necessary to determine appropriate dosages depending on the mode of administration (oral, parenteral, aerosol, etc.) and the particular virus being treated, no undue experimentation is required by one of ordinary skill in this art aware of the pharmacological activity of the active principles discussed herein. Determination of the effective amounts is within the skill in the art.

The present invention further includes salts or other derivatives of hypericin or pseudohypericin which retain their anti-viral activity. Salts in which the base is of the alkaline or amine type are particularly comprehended within the scope of the present invention.

In addition to the hypericin or pseudohypericin, the pharmaceutical compositions may contain suitable pharmaceutically acceptable carriers comprising excipients and auxiliaries which facilitate processing of the active compounds into preparations which can be used pharmaceutically. Preferably, the preparations, particularly those for oral administration, such as tablets, dragees and capsules, and also preparations which can be administered rectally, such as suppositories, as well as suitable solutions for administration by injection or orally, or for administration by means of an aerosol contain from about 0.1 to 99%, preferably from about 25-85% of active compound(s), together with the excipient.

The pharmaceutical preparations of the present invention are manufactured in a manner which is itself known, for example, by means of conventional mixing, granulating or dragee-making processes. Thus, pharmaceutical preparations for oral use can be obtained by combining the active compound(s) with solid excipients, optionally grinding a resulting mixture and processing the mixture of granules, after adding suitable auxiliaries, if desired or necessary, to obtain tablets or dragee cores.

Suitable excipients are, in particular, fillers such as sugars, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethylstarch, cross-linked polyvinyl pyrrolidone, agar, or algenic acid or a salt thereof, such as sodium alginate. Auxiliaries are, above all, flow-regulating agents and lubricants, for example, silica, talc, steric acid or salts thereof, such as magnesium stearate or calcium stearate, and/or polyethylene glycol. Dragee cores are provided with suitable coatings which, if desired, are resistant to gastric juices. For this purpose, concentrated sugar solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, are used. Dye stuffs or pigments may be added to the tablets or dragee coatings, for example, for identification or in order to characterize different combinations of active compound doses.

Other pharmaceutical preparations which can be used orally include push-fit capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, liquid paraffin, or liquid polyethylene glycols. In addition, stabilizers may be added.

Possible pharmaceutical preparations which can be used rectally include, for example, suppositories, which consist of a combination of the active compounds with a suppository base. Suitable suppository bases are, for example, natural or synthetic triglycerides, paraffin hydrocarbons, polyethylene glycols or higher alkanols. In particular, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate triglycerides. Aqueous injection suspensions may contain substances which increase the viscosity of the suspension including, for example, sodium carboxymethyl cellulose, sorbitol, and/or dextran. Optionally, the suspension may also contain stabilizers.

A preferred form of administration may be by aerosol spray, either as a means of systemic administration or as a means of topical administration to the mucous membranes and lungs. Any conventional aerosol excipients and propellants may be used for this purpose. For aerosol administration, the active principles in accordance with the present invention may be packaged in a pressurized container with an appropriate system of valves and actuators. Preferably, metered valves are used with the valve chamber being recharged between each actuation or dose, all as is well known in the art.

While the present description refers to the treatment of humans, the invention includes the treatment of all animals having viral infections. Foremost among such animals are humans; however, the invention is not intended to be so limiting. It is within the contemplation of the invention to treat any and all animals which may experience the beneficial effects of the invention.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology employed herein is for the purpose of description and not of limitation.

LEGEND TO FIGS.

FIG. 1: Delay of destruction of VSV infected cells in presence of different concentrations of hypericin (1).

Figure 2:
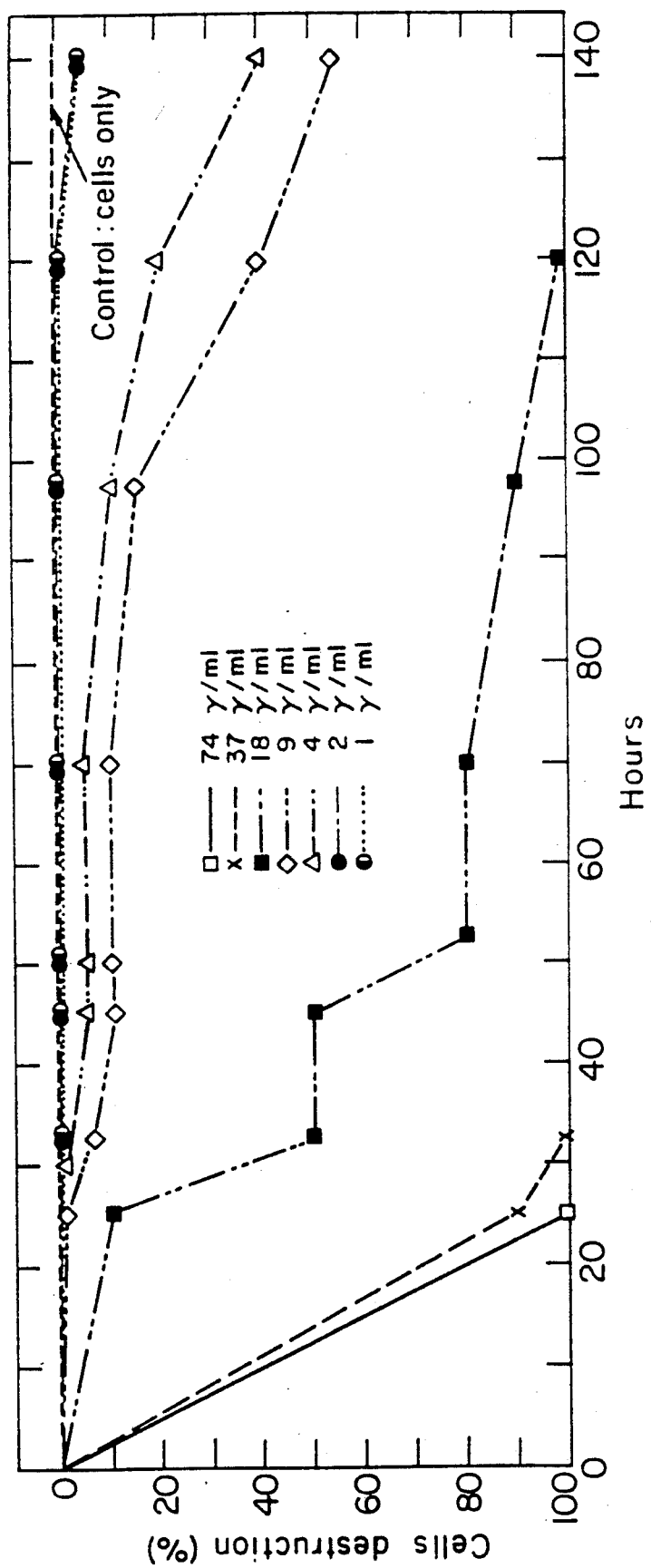
FIG. 2: Delay of destruction of uninfected cells in presence of different concentrations of hypericin (1).

FIG. 2: Delay of destruction of uninfected cells in presence of different concentrations of hypericin (1).

Figure 3:
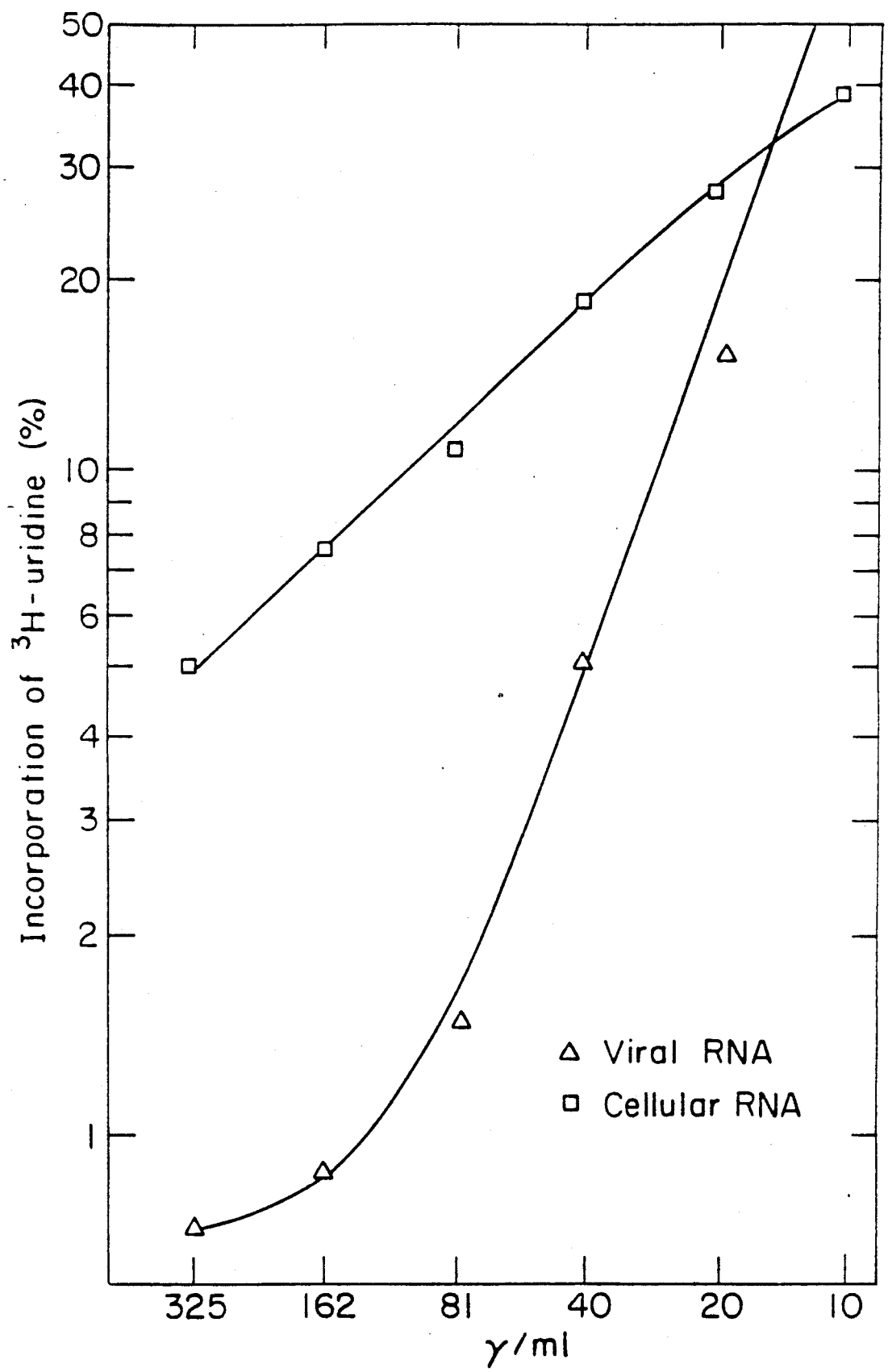
FIG. 3: Incorporation of $^3$H-uridine during RNA synthesis by Δ VSV (50 λ/ml) infected cells, and □ uninfected cells; measurements are made at different concentrations of pseudohypericin (2).

FIG. 3: Incorporation of $^3$H-uridine during RNA synthesis by: Δ VSV (50 λ/ml) infected cells, and □ uninfected cells; measurements are made at different concentrations of pseudohypericin (2).

Figure 4:
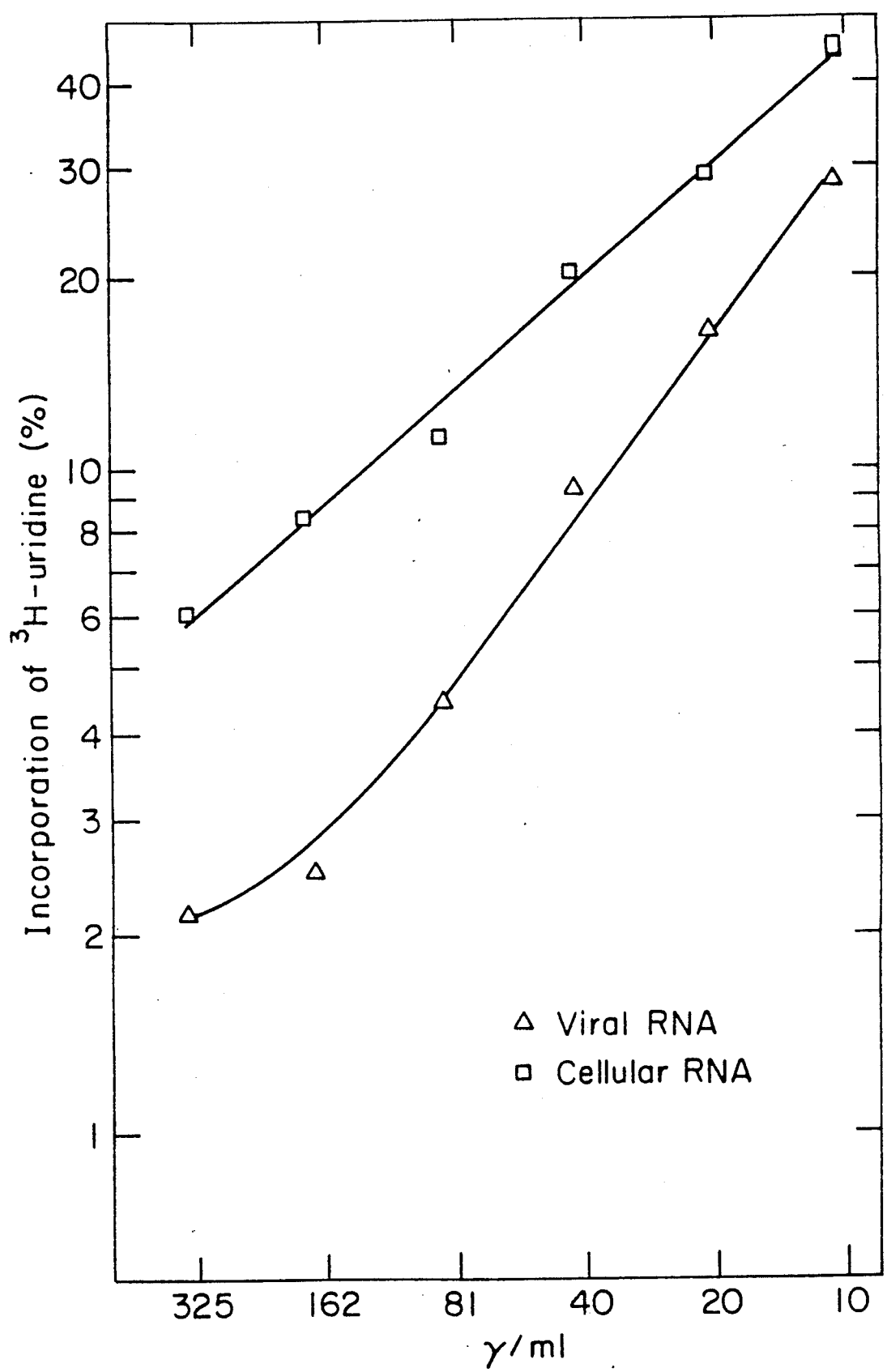
FIG. 4: Incorporation of $^3$H-uridine during RNA synthesis by: Δ VSV (100 λ/ml) infected cells, and □ uninfected cells; measurements are made at different concentrations of pseudohypericin (2).

FIG. 4: Incorporation of $^3$H-uridine during RNA synthesis by: Δ VSV (100 λ/ml) infected cells, and □ uninfected cells; measurements are made at different concentrations of pseudohypericin (2).

We claim:

1. An antiviral pharmaceutical composition for aerosol administration to animals, including humans, comprising, a propellent, a pharmaceutically acceptable aerosol excipient suitable to place the composition into form for aerosol administration and, as active ingredient, an antiviral effective quantity of a pure compound selected from the group consisting of hypericin, pseudohypericin, a pharmaceutically acceptable salt of hypericin or pseudohypericin, and mixtures thereof.

2. In a pressurized container for spraying unit dosages of pharmaceutical composition for aerosol administration to animals, including humans, comprising a container containing said composition under pressure and a valve, the improvement wherein said composition comprises a composition in accordance with claim 1.

3. A composition in accordance with claim 1, wherein said active ingredient is hypericin or a pharmaceutically acceptable salt thereof.

4. A composition in accordance with claim 1, wherein said active ingredient is pseudohypericin or a pharmaceutically acceptable salt thereof.

5. A composition in accordance with claim 1, wherein said active ingredient is a combination of hypericin, or a pharmaceutically acceptable salt thereof, and pseudohypericin, or a pharmaceutically acceptable salt thereof.

6. A pressurized container in accordance with claim 2, wherein in said composition said active ingredient is hypericin or a pharmaceutically acceptable salt thereof.

7. A pressurized container in accordance with claim 2, wherein said active ingredient is pseudohypericin or a pharmaceutically acceptable salt thereof.

8. A pressurized container in accordance with claim 2, wherein said active ingredient is a combination of hypericin, or a pharmaceutically acceptable salt thereof, and pseudohypericin, or a pharmaceutically acceptable salt thereof.

* * * * *